United States Patent [19]
Chaudhari et al.

[11] Patent Number: 5,817,295
[45] Date of Patent: Oct. 6, 1998

[54] ALCOHOL FREE MOUTHWASH

[75] Inventors: Atma Chaudhari; Heinrich Scheurer, both of Scarborough, Canada; Pauline Pan, Morris Plains; Frank Volpe, Kinnelon, both of N.J.

[73] Assignee: Warner-Lambert Company, Morris Plains, N.J.

[21] Appl. No.: 791,040

[22] Filed: Jan. 28, 1997

Related U.S. Application Data

[63] Continuation of Ser. No. 236,405, May 2, 1994, abandoned.

[51] Int. Cl.$^6$ ............................... A61K 7/16; A61K 7/26
[52] U.S. Cl. .................................. 424/49; 424/58
[58] Field of Search ............................ 424/49–58

[56] References Cited

U.S. PATENT DOCUMENTS

| | | | |
|---|---|---|---|
| 3,164,524 | 1/1965 | Fand et al. | 167/93 |
| 3,864,472 | 2/1975 | Pensak et al. | 424/54 |
| 3,876,759 | 4/1975 | Pensak et al. | 424/58 |
| 3,947,570 | 3/1976 | Pensak et al. | 424/54 |
| 4,550,018 | 10/1985 | Ambike et al. | 424/52 |
| 4,919,918 | 4/1990 | Cole et al. | 424/44 |
| 4,945,087 | 7/1990 | Talwar et al. | 514/60 |
| 4,992,259 | 2/1991 | Schiraldi et al. | 424/49 |
| 5,283,056 | 2/1994 | Chung et al. | 424/49 |
| 5,284,648 | 2/1994 | White et al. | 424/49 |
| 5,292,527 | 3/1994 | Konopa | 424/54 |
| 5,298,238 | 3/1994 | Hussein et al. | 424/49 |
| 5,320,863 | 6/1994 | Chung et al. | 426/650 |
| 5,348,750 | 9/1994 | Greenberg | 426/3 |
| 5,376,374 | 12/1994 | Zelaya | 424/195 |
| 5,389,360 | 2/1995 | Mobley et al. | 424/49 |
| 5,405,603 | 4/1995 | Mackles et al. | 424/49 |
| 5,405,604 | 4/1995 | Hall | 424/54 |
| 5,407,662 | 4/1995 | Mackles et al. | 424/49 |
| 5,407,664 | 4/1995 | Konopa | 424/54 |
| 5,496,539 | 3/1996 | Mobley et al. | 424/49 |
| 5,538,667 | 7/1996 | Hill et al. | 252/312 |
| 5,560,906 | 10/1996 | Scopari et al. | 424/54 |
| 5,585,343 | 12/1996 | McGee et al. | 512/1 |
| 5,628,986 | 5/1997 | Sanker et al. | 424/49 |
| 5,645,841 | 7/1997 | Hill et al. | 424/401 |
| 5,688,491 | 11/1997 | Shahidi | 424/49 |
| 5,707,610 | 1/1998 | Ibsen et al. | 424/49 |
| 5,733,530 | 3/1998 | Bacca et al. | 424/52 |

FOREIGN PATENT DOCUMENTS

| | | |
|---|---|---|
| 244363 | 11/1987 | European Pat. Off. . |
| 338978 | 10/1989 | European Pat. Off. . |
| 93/08792 | 5/1993 | WIPO . |
| 94/07477 | 4/1994 | WIPO . |
| 94/16674 | 8/1994 | WIPO . |

OTHER PUBLICATIONS

Listermint Mouthwash USPTO Reg. T.M. No. 1 808 737 Registered Dec. 7, 1993 first used in commerce Oct. 31, 1988.
Cool Mint Listerine Antiseptic Mouthwash USPTO Reg. T.M. No. 1 728 521 Registered Oct. 27, 1992 first used in commerce May 15, 1992.
Listermint Mouthwash and Gargle USPTO Reg TM. No. 956 233 Registered Mar. 27, 1973 first use in commerce Jan. 7, 1972.
Listerine Antiseptic USPTO Reg T.M. 240162 Registered Mar. 20, 1928 first used in commerce May 1, 1881.
Listerine Antiseptic USPTO Reg T.M. 85150 Registered Jan. 30, 1912 first used in commerce May 1, 1881.
Listerine Antiseptic USPTO Reg TM 45682 Registered Aug. 29, 1905 first used in commerce May 1, 1881.
Listerine Antiseptic Toothwash Reg T.M. 41413 Registered Nov. 3, 1903 first used in commerce May 1, 1881.

*Primary Examiner*—Shep K. Rose
*Attorney, Agent, or Firm*—Jean B. Barish; Evan J. Federman

[57] ABSTRACT

A pleasant-tasting, substantially alcohol-free oral mouthwash composition is effective in eliminating the bacteria and other oral microflora responsible for the production of plaque, periodontitis, gingivitis, gum disease and bad breath. The composition consists of a unique blend of the essential oils thymol or eucalyptol, methyl salicylate, menthol and tripartite blend of peppermint flavor oils that are dissolved in solution using a non-ionic surfactant blend.

25 Claims, No Drawings

ALCOHOL FREE MOUTHWASH

This is a continuation application of U.S. Ser. No. 08/236,405 filed on May 2, 1994, now abandoned.

FIELD OF INVENTION

The invention relates generally to oral mouthwashes for the prevention and elimination of bad breath as well as the reduction of oral microflora responsible for the development of plaque. Dental plaque can lead to tooth decay, gingivitis and other related gum disease. In particular, the present invention relates to an alcohol free mouthwash that is effective in preventing those problems and is pleasant tasting as well.

BACKGROUND OF THE INVENTION

Oral rinse and mouthwash compositions have been used by people for many years for the prevention of bad breath and for the elimination of bacteria and other oral microorganisms that are responsible not only for bad breath but also tooth decay, plaque and gum disease such as gingivitis and periodontitis. To this end mouthwashes in the past have been designed to clean the oral cavity, provide fresh breath and kill the harmful bacteria.

Conventional mouthwashes have always contained fairly high levels of ethyl alcohol with percentages ranging from approximately 10% up to about 30% by volume. Alcohol is used both as a disinfectant and as a solvent in which other additives such as astringents, fluorides, color additives, flavor oils, bactericidal actives and the like can be dissolved and then dispersed into solution. High levels of alcohol are generally used to provide a disinfection function since lower concentrations are sufficient to dissolve and disperse the various components into solution. Alcohol also provides a preservative role for the mouthwash during storage and use as well as enhancement of flavor oil organoleptic cues.

Understandably however, the use of alcohol has not been regarded as beneficial from an overall health standpoint. Many people cannot tolerate alcohol in any form and there is concern that young children in particular may be adversely affected by ingesting or inadvertently swallowing mouthwash compositions of this type. Senior citizens have also complained about problems related to gargling with such mouthwashes, and chronic exposure has been found to result in gum "burn" by the alcohol. Alcoholic mouthwashes often result in a "dry mouth" sensation, while recovering alcoholics cannot be subjected to alcohol in any form.

Obviously then, there is a substantial need for the development of a non-alcoholic mouthwash that continues to be effective in the prevention of bad breath, the killing of oral bacteria and the resultant reduction or elimination of plaque. Several attempts at formulating non-alcoholic mouthwash compositions can be found in the prior art. U.S. Pat. No. 5,292,527 to Konopa discloses a non-alcoholic, aqueous mouthwash composition comprising a dispersion system that consists of a non-ionic surfactant selected from the group comprising hydrogenated castor oils and a polyoxyethylene polyoxypropylene block copolymer having about 50% to about 90% ethylene oxide, a humectant and a cationic antimicrobial agent such as cetylpyridium chloride. The composition allegedly exhibits a homogeneous, uniform appearance and high degree of bactericidal efficacy.

U.S. Pat. No. 5,284,648 to White et. al. discloses an alcohol free, oral rinse and pre-rinse emulsion containing cleaning and coating compositions that are non-irritating and low foaming for maximum plaque disruption and removal. The cleaning effect is achieved using an aqueous system containing a mouth conditioner comprising polydimethylsiloxane emulsified in a surfactant such as a block copolymer of polyoxyethylene and polyoxybutylene.

U.S. Pat. No. 4,919,918 to Cole et. al. discloses a non-alcoholic effervescent mouthwash tablet for cleaning and disinfecting the oral cavity using surfactants to reduce the surface tension of the compound when placed in solution. A dry, effervescent tablet, the composition is hydrated in water and the surfactant further facilitates the dissolution and dispersion of the actives. The effervescence gives increased foaming action while the surfactant, selected from the group consisting of sodium lauryl sulfate, sodium n-laurylsarcosinate, sodium alksylsulfoacetate, sulfocolaurate and sulfated monoglyceride aids in the breakdown and removal of food and other debris that is adhered to the gums and teeth. Fluoride as well as antimicrobial and tarter control agents may also be employed.

U.S. Pat. No. 5,145,664 to Thompson discloses an alcohol-free mouthwash consisting of an aqueous based carrier containing sodium chloride, sodium bicarbonate, flavoring agents and a solubilizing agent consisting of a mixture of the partial lauric esters of sorbitol producing a solution that is substantially isotonic with the oral mucosa. U.S. Pat. Nos. 3,577,490, 3,629,468 and 3,518,343 all disclose effervescent tablet formulations which, when dissolved in water, provide alcohol free mouthwash solutions which utilize the effervescence action to "scrub clean" the teeth and gums.

Nowhere in the prior art is there any teaching or suggestion of a substantially alcohol-free mouthwash that can be manufactured and sold in conventional liquid form that provides effective antimicrobial action for the reduction of germs associated with plaque, bad breath and gingivitis. For purposes of the present invention, the term alcohol-free shall mean that alcohol is substantially absent, if not completely absent from the formulation. Minute or trace amounts below 1.0% may possibly be found as a result of the flavor oils used in the present invention, but these amounts are so low that they will not pose any health risk or noticeable bite or burn.

There are three basic types of mouthwash formulations commercially available. There are conventional mouthwashes which serve primarily to sweeten the breath with volatile flavor oils and are not really formulated to function in any other significant way such as providing antimicrobial action and/or removal of mouth debris. Pre-rinse formulations are a second type and are used immediately prior to brushing as a way of rendering deposited plaque or calculus more susceptible to removal from the teeth by brushing and abrasion. Finally, there are the gingivitis and tarter control formulations that contain antimicrobial actives such as phenols, sanguinaria, chlorhexidine and stannous fluoride and anti-tarter or plaque fighters such as sodium benzoate and the like.

In conventional alcohol-containing mouthwashes, the alcohol provides several functions. On the one hand, it provides antimicrobial activity and kills the bacteria and other microflora responsible for tooth decay, plaque and gum disease. It is also necessary as a solvent for most of the flavor oils and other water insoluble actives such as the essential oils. Without completely solubilizing these oils into solution, the mouthwash is also less aesthetically appealing as a clear or colorless composition cannot be obtained. Finally, alcohol acts as a preservative and prevents bacterial growth and spoilage within the bottle during its shelf life and during use. Therefore, merely removing the alcohol is not enough to provide an effective alcohol-free mouthwash. Other ingredients must be found to provide these functions. In those mouthwash compositions that are bactericidal for the prevention of plaque and gum disease, higher levels of alcohol are generally necessary to aid in the disinfection function. As a result, these oral formulations are both bitter tasting and impart an unpleasant alcohol burn or bite.

SUMMARY OF THE INVENTION

A substantially alcohol-free mouthwash provides effective breath freshening and antimicrobial oral hygiene for everyday use. The mouthwash composition is comprised of a unique mix of non-ionic and ionic surfactants, essential oils, flavor oils and other excipents that surprisingly and unexpectedly provide all the benefits of an alcohol-based composition without the inherent drawbacks.

DETAILED DESCRIPTION OF THE INVENTION

The substantially non-alcoholic mouthwash compositions of the present invention are useful in the germ kill of microorganisms responsible for plaque, gingivitis and other oral diseases caused by bacteria in the mouth while also providing breath freshening characteristics and are pleasant tasting with a smooth, cooling and lubricous mouth-feel. The mouthwash compositions are also well preserved and shelf-stable despite the absence of alcohol.

The mouthwash compositions of the present invention surprisingly and unexpectedly provide the aforementioned functions without the presence of alcohol through the use of a two-part blend of non-ionic and ionic surfactants and a unique mixture of flavor oils which combine to provide cooling and refreshing sensory notes while taste-masking the bitter, astringent taste of the antimicrobial actives. The compositions provide a healthy oral hygiene regimen for everyone, especially those who for one reason or another cannot tolerate the presence of alcohol.

The antimicrobial efficacy of the mouthwash compositions is attributed to the presence of what are known as essential oils, i.e., minor amounts of thymol or eucalyptol, menthol, eugenol and methyl salicylate. Thymol, $(CH_3)_2CHC_6H_3(CH_3)OH$ (isoprophy-m-cresol), is only slightly soluble in water but is soluble in alcohol and is one of the reasons alcohol was necessary in well established commercial mouthwashes such as Listerine® in the past. Methyl salicylate $(C_6H_4OHCOOCH_3)$ also known as wintergreen oil, additionally provides flavoring to the mouthwash together with its antimicrobial function. Eucalyptol $(C_{10}H_{18}O;$ cineol) is a terpene ether and provides a cooling, spicy taste. Eucalyptol may be used in place of thymol in certain formulations in the same amount if desired. Menthol $(CH_3C_6H_9(C_3H_7)OH;$ hexahydrathymol) also is only slightly soluble in alcohol, is fairly volatile, and in addition to any germ killing properties provides a cooling, tingling sensation. Eugenol $(C_3H_5C_6H_3(OH)OCH_3;$ 4-allyl-2-methoxyphenol) is soluble in alcohol and ether but only slightly soluble in water.

Thymol, or in its place eucalyptol, is incorporated into the formulations of the present invention in amounts of from about 0.001% w/v to about 0.08% w/v and preferably in an amount of about 0.02% w/v. Whereas eucalyptol may be used in place of thymol, it must be incorporated in slightly higher concentrations in a range of from approximately 0.01% w/v to about 2.0% w.v. Methyl salicylate is incorporated in an amount of from approximately 0.001% w/v to about 0.5% and preferably in an amount of approximately 0.1%. Menthol is incorporated into the mouthwash formulations of the present invention in an amount of approximately 0.001% w/v to about 0.10% w/v and preferably in an amount of about 0.06% w/v. Eugenol is incorporated in an amount of from about 0.001% w/v to about 0.06% w/v.

Surface active agents (surfactants) are organic materials which aid in the complete dispersion of the ingredients throughout the solution as well as dispersing the preparation throughout the oral cavity. Preferably, the surfactants incorporated are a blend of non-ionic and ionic surfactants which act together to solubilize the actives. The non-ionic surfactants are selected from the group known as poly (oxyethylene) poly(oxypropylene) block copolymers. Such copolymers are known commercially as poloxamers and are produced in a wide range of structures and molecular weights with varying contents of ethylene oxide. The non-ionic poloxamers according to the invention are non-toxic and acceptable as direct food additives. They are stable and readily dispersible in aqueous systems and are compatible with a wide variety of formulations and other ingredients for oral preparations. These surfactants should have an HLB (Hydrophilic-Lipophilic Balance) of between about 10 and 30 and preferably between 10 and 25.

Thus, non-ionic surfactants useful in this invention include poloxamers:

| | | | |
|---|---|---|---|
| 105 | 188 | 237 | 334 |
| 108 | 215 | 238 | 335 |
| 124 | 217 | 284 | 338 |
| 184 | 234 | 288 | 407 |
| 185 | 235 | 333 | |

Generally these polymers should constitute from about 0.01% w/v to about 8.0% w/v and preferably from about 0.25% to about 0.75% w/v. A particularly preferred poloxamer 105 which is incorporated in an amount of about 0.5%.

A second surfactant, sodium lauryl sulfate is ionic and is used in combination with the poloxamer to surprisingly solubilize the essential oils and flavor oils otherwise not soluble in aqueous systems. The surfactants also act to disperse the actives and flavors throughout the solution and enable the compositions to provide a clear, uniform appearance that is aesthetically more appealing. The sodium lauryl sulfate is incorporated in an amount of from approximately 0.05% w/v to about 2.0% w/v, and preferably is added in an amount of about 0.2% w/v.

One or more flavor oils may be used in the practice of the present invention. The amount of flavor oils used should comprise from about 0.2% w/v to about 2.5% w/v. In one embodiment of the present invention, three types of peppermint oil, natural, Far West (Redistilled, terpeneless) and Rose Mitchum are combined to provide a tripartite blend. This unique blend of flavor oils as mentioned before not only provides for a pleasant tasting mouthwash but also serves to taste mask the bitter tasting essential oil actives discussed above. All three are individually combined in substantially the same amount of from about 0.01% w/v to about 1.0% w/v and preferably, in an amount of from about 0.2% w/v to about 0.3% w/v. Combined, the tripartite blend is incorporated in the mouthwash composition in an amount of approximately 0.1% to about 2.0% and preferably in an amount of from about 0.5% to about 0.9%.

Together with this triple peppermint blend, the essential oil methyl salicylate, a wintergreen flavor oil, also provides a disinfecting function in this manner as well. Other flavor oils may be added to further modify or magnify the cooling minty taste of the peppermint. Suitable flavors in particular include oil of anise (0.01% to about 0.2% w/v) and benzyl alcohol (0.001% w/v to about 0.1% w/v). In one particular embodiment of the present invention, the mouthwash is not colorless and clear but a clear green and further includes spearmint oil (0.01% w/v to about 2.0% w/v) as an additional flavorant. Other flavors such as citrus oils, vanillin and the like may be incorporated to provide further taste variations.

Additional components may be added as in conventional mouthwashes of the prior art. Whereas some alcohol containing mouthwashes have a pH of about 7.0, removal of the alcohol requires the addition of preservatives which drops the pH to unacceptable levels. Buffer systems are then necessary to control the pH of the composition at optimal levels. This is accomplished generally through the addition of a weak acid and its salt or a weak base and its salt. Useful systems have been found to be sodium benzoate and benzoic acid in amounts of from approximately 0.01% to about 2.0% w/v and sodium citrate and citric acid in amounts of from about 0.001% w/v to about 2.0% w/v and preferably from about 0.1% to about 0.2% w/v respectively. Preferably the buffers are incorporated in amounts that maintain the pH at levels of from approximately 3.5 to about 6.5 and more preferably, from about 4.8 to 5.2. Without being bound to any theory, it is believed that these pH levels provide the essential oils with an environment that maximizes their germ killing efficacy.

Other ingredients include those known and used in the art. A humectant such as polyethylene glycol may be added as an additional solubilizer for the flavor oils and these also provide texture to the composition. These are incorporated in amount of approximately 0.3% w/v to about 0.6% w/v and preferably about 0.5% w/v. Softeners such as glycerin are added to enhance the lubricous mouthfeel of the mouthwash as it is used and to provide a refreshing, moist, organoleptic feeling thereafter. Glycerin is incorporated in amounts of approximately 1.0% w/v to about 10.0% w/v and preferably in an amount of about 7.5%. Sweeteners such as aspartame or sodium saccharin may be added for better taste in amounts of from about 0.005% w.v to about 1.0% w.v and preferably in an amount of approximately 0.05% w/v. Zinc chloride may be added as an astringent for a "disinfecting cleaning" feeling in an amount of from about 0.0025% w/v to about 0.0075% w/v. And although the mouthwash formulations of the present invention are substantially clear and colorless, acceptably approved food dyes may be used to color the mouthwash. These may be selected from the long list of FD & C dyes and in particular may be incorporated to provide the spearmint green formulation discussed infra. Suitable dyes for this purpose include FD & C yellow #5, yellow #10 and FD & C green #3 and these are added in amounts of from about 0.0003% w/v to about 0.0005% w.v or preferably from approximately 0.000035% w/v to about 0.00045% w/v. Water is added to q.s. and the formulation may then be bottled and packaged for shipping.

Alternatively, the mouthwash compositions of the present invention may be formulated in a dry powder or liquid concentrate form. In such embodiments, the water added to q.s. the volume to the necessary total is not added in order to prepare the liquid concentrate or what water is present is removed using standard evaporation procedures known in the art to prepare the dry powder form. Both may then have water added at a later date when ready for use. Such forms are advantageous for storage and shipping.

The following examples are provided to more specifically recite the elements and preparation of the mouthwash formulation of the present invention. They are for illustrative purposes only, and it is recognized that many variations may be formulated to change or alter the composition to a degree. It is understood however that such alterations will still be considered to fall within the spirit and scope of the invention as recited by the claims that follow.

EXAMPLE I

The following ingredients were assembled together in their respective amounts.

| | Ingredients | Percent w/v | Amount 100 liter |
|---|---|---|---|
| 1. | Sodium Lauryl Sulphate | .210 | 210.0 g. |
| 2. | Benzoic Acid | 0.025 | 25.0 g. |
| 3. | Sodium Saccharin | 0.050 | 50.0 g. |
| 4. | Zinc Chloride | 0.005 | 5.0 g. |
| 5. | Sodium Benzoate | 0.180 | 180.0 g. |
| 6. | Glycerin 99% | 7.500 | 7.5 kg. |
| 7. | Thymol | 0.020 | 20.0 g. |
| 8. | l-Menthol | 0.060 | 60.0 g. |
| 9. | Oil of Peppermint Natural Brand | 0.030 | 30.0 g. |
| 10. | Oil of Peppermint Far West Terpeneless | 0.020 | 20.0 g. |
| 11. | Oil of Peppermint Rose Mitchum | 0.030 | 30.0 g. |
| 12. | Oil of Anise | 0.014 | 14.0 g. |
| 13. | Eugenol | 0.006 | 6.0 g. |
| 14. | Benzol Alcohol | 0.040 | 40.0 g. |
| 15. | Methyl Salicylate | 0.110 | 110.0 g. |
| 16. | Polyethylene Glycol | 0.500 | 500.0 g. |
| 17. | Pluronic 105 | 0.500 | 500.0 g. |
| 18. | Deionized Water | q.s. to | 100.0 L |
| 19. | Benzoic Acid to adjust pH | q.s. | q.s. |
| 20. | Sodium Benzoate to adjust pH | q.s. | q.s. |

Ten liters of deionized water were mixed with 7.5 kg. of glycerin in a 100 liter container using a high shear mixer. Sodium lauryl sulfate was then added and mixing continued until all the ingredients were dissolved. Once a clear solution was achieved, the saccharin, zinc chloride and sodium benzoate were added and mixed until dissolved.

The essential oils and flavor oils were placed in a 500 ml. container and mixed until they become uniform. The benzoic acid was then added and mixed until the solution once again became clear. The polyethylene glycol was first preheated to 40° C. and this was combined in still a third vessel with the poloxamer 105 which had been heated to 45° C.–60° C. The surfactants were then added to the essential oil/flavor oils mixture and thoroughly dispersed. Subsequently, the glycerin, sodium lauryl sulfate and buffers combination that was previously mixed is added to the main batch and this was mixed for at least 30 minutes. Water was then added to q.s. the solution to 100 liters and the pH is adjusted, if necessary, using the sodium benzoate or benzoic acid buffers depending on whether the pH needs to be lowered or raised.

The colorless mouthwash had a pleasingly fresh, peppermint taste with a pH of about 5.0. Its specific gravity was 1.021.

EXAMPLE II

The mouthwash formulation set forth in Example I was evaluated in vitro against oral malodor-causing bacteria, plaque-causing bacteria and an oral pathogenic yeast in order to prove the alcohol-free mouthwash is effective against microflora of the oral cavity. These species include

*Fusobacterium nucleatum* (ATCC 10953); *Prevotella melaninoaenica* (ATCC 25895); *Candida albicans* (ATCC 18804); *Streptococcus mutans* (ATTC 25175); *Actinomyces viscosus* (ATCC $T_{14}V$); *Streptococcus sanguis* (ATCC 10558); and *Pseudomonas aeruginosa* (ATCC 10145). A series of Bahn kill kinetic studies were conducted in order to determine the time it takes to kill the microorganisms to prove breath freshening and efficacy against plaque and gum disease associated bacteria. The alcohol free mouthwash formulations of the present invention, clear peppermint and green spearmint, were compared against several well known commercial brands.

As set forth in Table 1, the data demonstrate that the alcohol-free mouthrinse of the present invention were equally efficacious against representative Gram negative and Gram positive bacteria. Kill times of <0.5 min. for *S. mutans* and *A. viscosus* indicate bactericidal efficacy against plaque associated bacteria and <0.5 min. kill time for *E. nucleatum* and *P. melaninogenicus* also confirms effectiveness against oral malodor causing organisms.

significantly better than the commercial blue (4) and the control (7) in reducing oral malodor. There was no statistically significant differences between all four treatment groups at 240 minutes post-baseline.

EXAMPLE IV

The following ingredients were combined together according to the process of Example I in order to prepare a liquid concentrate of the mouthwash of the present invention.

| Ingredients | Percent w/v | Amount 20 liter |
|---|---|---|
| 1. Sodium Lauryl Sulfate | 1.050 | 210.0 g. |
| 2. Benzoic Acid | 0.125 | 25.0 g. |
| 3. Sodium Saccharin | 0.250 | 50.0 g. |
| 4. Zinc Chloride | 0.025 | 5.0 g. |
| 5. Sodium Benzoate | 0.900 | 180.0 g. |

TABLE 1

BAHN TESTS RESULTS

| PRODUCT NAME | *F. nucleatum* #10953 | *P. melaninogenicus* #25845 | *S. mutans* #25175 | *A. viscosus* #$T_{14}V$ | *S. sanguis* #10558 | *P. aeruginosa* #10145 | *C. albicans* #18804 |
|---|---|---|---|---|---|---|---|
| Sample 1 | <0.5 min. | <0.5 min. | <0.5 min. | <0.5 min. | <0.5 min. | <0.5 min. | <2.0 min. |
| Sample 2 | <0.5 min. | <0.5 min. | <0.5 min. | <0.5 min. | <0.5 min. | <0.5 min. | <1.0 min. |
| Sample 3 | <0.5 min. | <0.5 min. | <0.5 min. | <0.5 min. | <0.5 min. | <0.5 min. | <0.5 min. |
| Sample 4 | <0.5 min. | <0.5 min. | <0.5 min. | <0.5 min. | <0.5 min. | <0.5 min. | <0.5 min. |
| Sample 5 | <0.5 min. | <0.5 min. | <0.5 min. | <0.5 min. | <0.5 min. | <0.5 min. | <0.5 min. |
| Sample 6 | <0.5 min. | <0.5 min. | <0.5 min. | <0.5 min. | <0.5 min. | <0.5 min. | <0.5 min. |
| Sample 7 | <0.5 min. | <0.5 min. | <0.5 min. | <0.5 min. | <0.5 min. | <0.5 min. | <5.0 min. |
| Sample 8 | <0.5 min. | <0.5 min. | <0.5 min. | <0.5 min. | <0.5 min. | <0.5 min. | <0.5 min. |
| Sample 9 | No Kill | No Kill | No Kill | No Kill | No Kill | No Kill | No Kill |

Sample (1) Alcohol Free Peppermint
Sample (2) Alcohol Free Spearmint
Sample (3) Commercial Alcohol Free Clear
Sample (4) Commercial Blue (16.6% alc.)
Sample (5) Commercial Green (18.9% alc.)
Sample (6) Reduced Alcohol Green (6.65% alc.)
Sample (7) Control (26.9% alc.)
Sample (8) Negative Control (Deionized water)

EXAMPLE III

A clinical malodor study was performed to compare the degree and duration of effectiveness of the compositions of the present invention and a commercial alcohol containing cosmetic product to that of a placebo control for the reducing human intrinsic breath malodor.

There were statistically significant differences between all four treatment groups at 30 minutes post-baseline. The treatment with the lowest mean malodor scope was the alcohol-free spearmint composition of the present invention (2), followed by the alcohol-free peppermint composition of the present invention (1) followed by commercial blue (4) and the control (7) in ascending order of mean malodor scores. At 60, 90 and 120 minutes post-baseline, both the alcohol-free peppermint and spearmint compositions of the present invention had statistically significantly lower mean malodor scores than both the commercial blue (4) and the control (7), but there were no statistically significant differences between the alcohol-free peppermint (1) and spearmint compositions (2) of the present invention and the commercial blue (4) and the control (7). At 180 minutes post-baseline, only the alcohol-free peppermint and spearmint compositions of the present invention was statistically -continued

| Ingredients | Percent w/v | Amount 20 liter |
|---|---|---|
| 6. Glycerin 99% | 37.500 | 7.5 kg. |
| 7. Thymol | 0.100 | 20.0 g. |
| 8. l-Menthol | 0.300 | 60.0 g. |
| 9. Oil of Peppermint Natural Blend | 0.150 | 30.0 g. |
| 10. Oil of Peppermint Far West | 0.100 | 20.0 g. |
| 11. Oil of Peppermint Rose Mitchum | 0.150 | 30.0 g. |
| 12. Oil of Anise | 0.070 | 14.0 g. |
| 13. Eugenol | 0.030 | 6.0 g. |
| 14. Benzyl Alcohol | 0.200 | 40.0 g. |
| 15. Methyl Salicylate | 0.550 | 110.0 g. |
| 16. Polyethylene Glycol 600 | 2.500 | 500.0 g. |
| 17. Pluronic 105 | 2.500 | 500.0 g. |
| 18. Deionized water | q.s. to | 20.0 liter |
| 19. Benzoic Acid to adjust pH | q.s. | q.s. |
| 20. Sodium Benzoate to adjust pH | q.s. | q.s. |

The resulting "concentrate" has a pleasant fresh peppermint taste, and showed increased antimicrobial activity.

What we claim is:

1. An alcohol-free mouthwash comprising:

thymol in an amount from 0.001% w/v to about 0.08% w/v;

methyl salicylate in an amount from 0.001% w/v to about 0.05% w/v;

menthol in an amount from 0.001% w/v to about 0.1% w/v;

a poly(oxyethylene)-poly(oxyproplyene) block copolymer having an average molecular weight of no more than about 12,000 in an amount from 0.01% w/v to about 8.0% w/v;

sodium lauryl sulfate in an amount from 0.05% w/v to about 2.0% w/v; and another flavor oil.

2. The alcohol-free mouthwash according to claim 1 wherein the poly(oxyethylene)-poly(oxyproplyene) block copolymer is in an amount from about 0.25% w/v to about 0.75% w/v.

3. The alcohol-free mouthwash according to claim 1 wherein the sodium lauryl sulfate is in an amount of about 0.2% w/v.

4. The alcohol-free mouthwash according to claim 1 wherein the flavor oil comprises at least one peppermint oil.

5. The alcohol-free mouthwash according to claim 4 wherein the at least one peppermint oil is in an amount from about 0.1% w/v to about 1.0% w/v.

6. The alcohol-free mouthwash according to claim 4 wherein the at least one peppermint oil comprises a blend of three peppermint oils.

7. The alcohol-free mouthwash according to claim 6 wherein the peppermint oils are incorporated in a total amount of from about 0.01% w/v to about 2.0% w/v.

8. The alcohol-free mouthwash according to claim 7 wherein the peppermint oils are incorporated in a total amount of from about 0.5% w/v to about 0.9% w/v.

9. The alcohol-free mouthwash according to claim 1 wherein the flavor oil comprises spearmint oil.

10. The alcohol-free mouthwash according to claim 9 wherein the spearmint oil is in an amount from about 0.01% w/v to about 2.0% w/v.

11. The alcohol-free mouthwash according to claim 1 further comprising at least one additive selected from the group consisting of buffers, sweeteners, FD & C dyes, humectants, softeners and astringents.

12. The alcohol-free mouthwash according to claim 1 further comprising eugenol in an amount from 0.001% w/v to about 0.06% w/v.

13. An alcohol-free mouthwash comprising:

eucalyptol in an amount from 0.01% w/v to about 2.0% w/v;

methyl salicylate in an amount from 0.001% w/v to about 0.05% w/v;

menthol in an amount from 0.001% w/v to about 0.1% w/v;

a poly(oxyethylene)-poly(oxyproplyene) block copolymer having an average molecular weight of no more than about 12,000 in an amount from 0.01% w/v to about 8.0% w/v;

sodium lauryl sulfate in an amount from 0.05% w/v to about 2.0% w/v; and another flavor oil.

14. The alcohol-free mouthwash according to claim 13 wherein the poly(oxyethylene)-poly(oxyproplyene) block copolymer is in an amount from about 0.25% w/v to about 0.75% w/v.

15. The alcohol-free mouthwash according to claim 13 wherein the sodium lauryl sulfate is in an amount of about 0.2% w/v.

16. The alcohol-free mouthwash according to claim 13 wherein the flavor oil comprises at least one peppermint oil.

17. The alcohol-free mouthwash according to claim 16 wherein the at least one peppermint oil is in an amount from about 0.1% w/v to about 1.0% w/v.

18. The alcohol-free mouthwash according to claim 17 wherein the at least one peppermint oil comprises a blend of three peppermint oils.

19. The alcohol-free mouthwash according to claim 18 wherein the peppermint oils are incorporated in a total amount of from about 0.01% w/v to about 2.0% w/v.

20. The alcohol-free mouthwash according to claim 19 wherein the peppermint oils are incorporated in a total amount of from about 0.5% w/v to about 0.9% w/v.

21. The alcohol-free mouthwash according to claim 13 wherein the flavor oil comprises spearmint oil.

22. The alcohol-free mouthwash according to claim 21 wherein the spearmint oil is in an amount from about 0.01% w/v to about 2.0% w/v.

23. The alcohol-free mouthwash according to claim 13 further comprising at least one additive selected from the group consisting of buffers, sweeteners, FD & C dyes, humectants, softeners and astringents.

24. The alcohol-free mouthwash according to claim 1 further comprising eugenol in an amount from 0.001% w/v to about 0.06% w/v.

25. An alcohol-free mouthwash comprising:

thymol in an amount from about 0.02% w/v;

methyl salicylate in an amount from about 0.1% w/v;

menthol in an amount from about 0.6% w/v;

a poly(oxyethylene)-poly(oxyproplyene) block copolymer having an average molecular weight of no more than about 12,000 in an amount from 0.01% w/v to about 8.0% w/v;

sodium lauryl sulfate in an amount from 0.05% w/v to about 2.0% w/v; and another flavor oil.

* * * * *

UNITED STATES PATENT AND TRADEMARK OFFICE
CERTIFICATE OF CORRECTION

| | | |
|---|---|---|
| PATENT NO. | : 5,817,295 | Page 1 of 1 |
| APPLICATION NO. | : 08/791040 | |
| DATED | : October 6, 1998 | |
| INVENTOR(S) | : Atma Chaudhari et al. | |

It is certified that error appears in the above-identified patent and that said Letters Patent is hereby corrected as shown below:

Column 9, line 8, replace "0.05" with --0.5--.

Column 9, line 56, replace "0.05" with --0.5--.

Column 10, lines 45-47, replace "from" with --of-- (all occurrences).

Signed and Sealed this

Twenty-third Day of February, 2010

David J. Kappos
*Director of the United States Patent and Trademark Office*